United States Patent
Shapiro et al.

[19]

[11] Patent Number: 5,957,866
[45] Date of Patent: Sep. 28, 1999

[54] APPARATUS AND METHODS FOR ANALYZING BODY SOUNDS

[75] Inventors: Joseph Isaac Shapiro, Aurora; Howard David Weinberger, Denver, both of Colo.

[73] Assignee: University Technology Corporation, Boulder, Colo.

[21] Appl. No.: 08/746,738

[22] Filed: Nov. 15, 1996

Related U.S. Application Data

[63] Continuation-in-part of application No. 08/498,673, Jul. 3, 1995, Pat. No. 5,687,738.
[51] Int. Cl.$^6$ .......................................... A61B 7/00
[52] U.S. Cl. .......................... 600/586; 600/528; 600/529; 600/481
[58] Field of Search .................... 600/509, 513, 600/514, 481, 483, 484, 528, 529, 586; 128/920, 928, 493

[56] References Cited

U.S. PATENT DOCUMENTS

| | | |
|---|---|---|
| 4,594,731 | 6/1986 | Lewkowicz .............................. 381/67 |
| 4,720,866 | 1/1988 | Elias et al. .............................. 381/67 |
| 4,765,321 | 8/1988 | Mohri . |
| 4,792,145 | 12/1988 | Eisenberg et al. . |
| 4,991,581 | 2/1991 | Andries .................................. 600/528 |
| 5,002,060 | 3/1991 | Nedivi . |
| 5,010,889 | 4/1991 | Bredesen et al. . |
| 5,025,809 | 6/1991 | Johnson et al. . |
| 5,213,108 | 5/1993 | Bredesen et al. . |
| 5,218,969 | 6/1993 | Bredesen et al. . |
| 5,301,679 | 4/1994 | Taylor . |
| 5,337,752 | 8/1994 | Reeves . |

Primary Examiner—Lee Cohen
Assistant Examiner—Bryan K. Yarnell

[57] ABSTRACT

Apparatus for assisting an operator to diagnose physical conditions in a patient by collecting and analyzing cyclical body sounds such as heart beat, peripheral vessel sounds, or breath sounds. Several cycles of data are collected and digitized. Each cycle is converted to the frequency domain and phase fixed. Then all of the frequency converted and phase fixed cycles are signal averaged together, and the results displayed to the operator. The cycles may be sorted according to respiratory cycle and averaged in two groups. The cycles may be gated according to the patients ECG. The apparatus may suggest diagnoses or further maneuvers to be performed.

31 Claims, 18 Drawing Sheets

FIG. 9

HEART SOUNDS

| ASCULTATION | ABNORMALITY | LESION | CONFIRMATION |
|---|---|---|---|
| S1 | LOUD 1 | MITRAL STENOSIS | ASSOCIATED MURMUR AND OS |
|  | SOFT 1 | MITRAL REGURGITATION | ASSOCIATED MURMUR<br>HAND GRIP |
| S2 | LOUD A2 | AORTIC REGURGITATION | ASSOCIATED MURMUR(S)<br>HAND GRIP |
|  |  | HYPERTENSION | CLINICAL FINDINGS |
|  | SOFT A2 | AORTIC STENOSIS | ASSOCIATED MURMUR (SEM) |
| S2 | A2 P2 INTERVAL DOES NOT VARY WITH RESPIRATION | ATRIAL SEPTAL DEFECT | SUGGEST ECHOCARDIOGRAM LOOK FOR ASSOCIATED FINDINGS WHICH SUGGEST PULMONARY HYPERTENSION |

| MURMURS | | | |
|---|---|---|---|
| TIMING | FREQUENCY | LESION | CONFIRMATION |
| SYSTOLE (STARTS AFTER S1 AND ENDS BEFORE S2) | MID-HIGH | AORTIC STENOSIS | ASSOCIATED EJECTION CLICK |
| TIMING IS FAIRLY CONSTANT | | VS PULMONIC STENOSIS VS. INNOCENT FLOW MURMUR | HAND GRIP/VALSALVA LOCATION/RADIATION |
| SYSTOLE (AS ABOVE) | MID-HIGH | MITRAL PROLAPSE | VARIABLE TIMING CLICK |
| TIMING MAY VARY | | WITH REGURGITATION | HAND GRIP/VALSALVA |
| SYSTOLE (AS ABOVE) | MID-HIGH | TRICUSPID REGURGITATION | LOUDEST AT LSB INCREASES WITH INSPIRATION |
| PAN SYSTOLIC | HIGH | MITRAL REGURGITATION | LOUDEST OVER APEX INCREASES WITH HAND GRIP |
| EARLY DIASTOLE | HIGH | AORTIC REGURGITATION VS PULMONIC REGURGITATION | ASSOCIATED MURMURS LOCATION WHERE MURMUR IS LOUDEST HAND GRIP/VALSALVA RESPIRATION DEPENDANCE |

FIG. 9 (cont.)

| | EXTRA SOUNDS | | | |
|---|---|---|---|---|
| TIMING | FREQUENCY | LESION | CONFIRMATION | |
| EARLY SYSTOLE | HIGH | AORTIC STENOSIS | ASSOCIATED MURMUR AND OS | |
| CONSTANT | HIGH | EJECTION CLICK | HAND GRIP/VALSALVA | |
| EARLY SYSTOLE | HIGH | MITRAL PROLAPSE | ASSOCIATED MURMUR(S) | |
| VARIABLE | HIGH | CLICK | HAND GRIP/VALSALVA | |
| EARLY DIASTOLE | HIGH | MITRAL STENOSIS OPENING SNAP (OS) | ASSOCIATED MURMUR DIASTOLIC RUMBLE | |
| EARLY DIASTOLE | LOW | THIRD HEART SOUND | LOUDEST OVER APEX | |
| LATE DIASTOLE | LOW | FOURTH HEART SOUND | LOUDEST OVER APEX, TIMING RELATED TO P WAVE ON ECG | |

FIG. 9 (cont.)

EXAMPLES OF DIAGNOSTIC APPROACH – BREATH SOUNDS

| TIMING | FREQUENCY | LOCATION | SOUND/LESION | CONFIRMATION |
|---|---|---|---|---|
| END-INSPIRATION | LOW PITCHED | PERIPHERAL | RALES/HEART FAILURE | S3 HEART SOUND, NO ATTENTION OF SPOKEN OR WHISPERED SOUNDS |
| END-INSPIRATION | LOW PITCHED | PERIPHERAL | RALES/PNEUMONIA | SPOKEN AND WHISPERED SOUNDS LOUDER AND CLEARER |
| INSPIRATION AND EXPIRATION | HIGH PITCHED | TRACHEA AND LARGE BRONCHI | NORMAL/NORMAL | |
| INSPIRATION AND EXPIRATION | LOW PITCHED | PERIPHERAL | NORMAL/NORMAL | |
| EXPIRATION | HIGH PITCHED | PERIPHERAL | WHEEZES/OBSTRUCTIVE LUNG DISEASE (ASTHMA) | INCREASE WITH FORCED EXPIRATION |
| INSPIRATION AND EXPIRATION | HIGH PITCHED | PERIPHERAL | "COARSE BREATH SOUNDS"/PULMONARY CONSOLIDATION (I.E. PNEUMONIA) | SPOKEN AND WHISPERED SOUNDS LOUDER AND CLEARER |
| INSPIRATION AND EXPIRATION | DECREASED INTENSITY | PERIPHERAL | EMPHYSEMA | |
| INSPIRATION AND EXPIRATION | DECREASED TO ABSENT | BASES | PLEURAL EFFUSION | EVIDENCE OF CONSOLIDATION ABOVE EFFUSION |
| INSPIRATION AND EXPIRATION | LOW PITCHED, LOUD | VARIABLE | PLEURAL FRICTION RUB | |

FIG. 10

EXAMPLES OF DIAGNOSTIC APPROACH – PERIPHERAL VESSEL SOUNDS

| TIMING | FREQUENCY | LOCATION | SOUND/LESION | CONFIRMATION |
|---|---|---|---|---|
| SYSTOLIC | LOW PITCHED | FEMORAL ARTERIES | SYSTOLIC BRUIT/NORMAL VARIANT | PHYSICAL EXAMINATION DETECTION OF GOOD PULSES MORE PERIPHERALLY |
| SYSTOLIC | HIGH PITCHED | FEMORAL OR OTHER PERIPHERAL ARTERY | SYSTOLIC BRUIT/SUSPECT STENOSIS | PHYSICAL EXAMINATION DETECTION OF POOR PULSES PERIPHERALLY. ULTRASOUND MAY BE INDICATED |
| SYSTOLIC AND DIASTOLIC | HIGH PITCHED | FEMORAL OR OTHER PERIPHERAL VESSEL | BRUIT/SUSPECT STENOSIS OR AV FISTULLA | PHYSICAL EXAMINATION DETECTION OF POOR PULSES PERIPHERALLY. ULTRASOUND MAY BE INDICATED |
| SYSTOLIC | LOW PITCHED | CAROTID | SYSTOLIC BRUIT/SUSPECT STENOSIS | EXCLUDE TRANSMITTED HEART SOUNDS. CONSIDER ULTRASOUND. |
| SYSTOLIC AND DIASTOLIC | HIGH PITCHED | CAROTID | BRUIT/SUSPECT CRITICAL STENOSIS | EXCLUDE TRANSMITTED HEART SOUNDS. CONSIDER ULTRASOUND. |
| SYSTOLIC AND DIASTOLIC | LOW PITCHED | HEMODIALYSIS AV FISTULLA | BRUIT/NORMAL | |
| SYSTOLIC AND DIASTOLIC | HIGH PITCHED | HEMODIALYSIS AV FISTULLA | BRUIT/SUSPECT STENOSIS | CONSIDER FISTULLAGRAM |

FIG. 11

APPARATUS AND METHODS FOR ANALYZING BODY SOUNDS

This application is a continuation in part of patent application Ser. No. 08/498,673 filed on Jul. 3, 1995, now U.S. Pat. No. 5,687,738, for Apparatus and Methods for Analyzing Heart Sounds.

BACKGROUND OF THE INVENTION

1. Field of the Invention

The present invention relates to apparatus and methods for analyzing body sounds. More particularly, the present invention relates to visual and computer assisted analysis of digitized body sounds.

2. Description of the Prior Art

The normal human heart is a four chambered structure, shown schematically in FIG. 1. It is arbitrarily divided into a right side (patient's right side) which accepts deoxygenated blood returning from the body through the venae cavae and pumps this blood into the lungs through the pulmonary artery. The lungs re-oxygenate the blood and excrete carbon dioxide. The re-oxygenated blood returns to the left side of the heart through the pulmonary veins and is pumped to the body through the aorta.

Both the right side and the left side of the heart have ventricles which actively pump blood through the contraction phase of the cardiac cycle (called systole) and atria which function to assist ventricular filling during the relaxation phase of the cardiac cycle (called diastole). On the right side of the heart, the tricuspid valve separates the right atrium and ventricle. The pulmonic valve separates the right ventricle and pulmonary artery. On the left side of the heart, the mitral valve separates the left atrium and ventricle, and the aortic valve separates the left ventricle and aorta.

Normal heart sounds are produced by the closure of the valves separating the atria from the ventricles (called the first heart sound, S1) and the subsequent closure of the valves separating the ventricles from their attached arteries (called the second heart sound, S2). The first heart sound, S1, has two components, T1 and M1. T1 is caused by the closure of the tricuspid valve, between the right atrium and right ventricle. M1 is caused by the closure of the mitral valve, between the left atrium and the left ventricle.

Similarly, the second heart sound, S2, has two components, A2 and P2. A2 is caused by closure of the aortic valve, between the left ventricle and aorta, and P2 is caused by closure of the pulmonic valve between the right ventricle and pulmonary artery. In a normal individual, mitral valve closure (M1) precedes tricuspid valve closure (T1) slightly. Aortic valve closure (A2) normally precedes pulmonic valve closure (P2) by a varying amount, depending upon the phase of the respiratory cycle. Normally, A2 precedes P2 by a longer period during inspiration than during expiration. All of these normal heart sounds are within the low frequency end of the human hearing range, falling between 30 and 250 Hz in frequency.

Abnormal heart sounds may be produced by the rapid filling of dilated ventricles, producing a third heart sound called S3, as well as by the contraction of the left atrium against a non-compliant left ventricle, producing a fourth heart sound called S4. Other abnormal heart sounds and murmurs may be produced by a variety of different pathological conditions.

The timing of abnormal hearts sounds relative to other heart sounds, to the respiratory cycle, and to the electrical impulses causing the heart to beat, is important in diagnosing the condition causing the abnormal sounds. FIG. 2 shows the relationship between the electrical impulse (normally detected by an electrocardiogram or ECG), the respiratory cycle, and normal heart sounds. Ventricular excitation is detected by the QRS complex of the ECG. When the ventricles are electrically excited, contraction occurs which results in increases in ventricular pressure. When the pressure in the left and right ventricles exceed that in their corresponding atria, closure of the mitral valve (M1) and the tricuspid valve (T1) occur, respectively. Usually, M1 and T1 overlap, so that S1 is one continuous sound rather than being split.

When ventricular contraction ceases and relaxation of the ventricular muscle occurs, pressure decreases in the ventricle. When the pressure in the left and the right ventricles falls below that of the aorta and pulmonary artery, respectively, aortic closure (A2) and pulmonic closure (P2) occur. The sum of A2 and P2 form the second heart sound (S2). S2 is usually split into separate, identifiable A2 and P2 sounds. The period between A2 and P2 is normally greater when the patient is inhaling than when the patient is exhaling.

Changes in the timing relationship or intensity of these normal sounds can indicate a physical problem. The existence of extra, abnormal heart sounds also frequently indicates some physical pathology. Various clues assist the physician in determining what condition is causing the extra sound. Frequency and pitch of extra sounds, their timing and duration, and their intensity are all related to their cause. Physiologic maneuvers, such as hand grip and valsalva (expiration against a closed glottis), which alter the amount of venous return as well as left ventricular after load, can be used to accentuate or diminish the intensity of some abnormal heart sounds and murmurs, and can, thus, be used to aid in differential analysis.

Normally, blood flow is not audible through peripheral arteries such as the carotid arteries (in the neck), the abdominal arteries (supplying the kidneys, intestines, etc.) and the extremities (e.g. femoral arteries). However, when these vessels become narrowed (stenosed) by pathological processes (e.g. atheromatous plaques) or flow is increased by the development of a shunt or fistula (e.g. hemodialysis access), then blood flow through these arteries may become audible. In general, the pitch or frequency of the sounds from such flow will correlate with the severity of the narrowing. Moreover, the sound of flow during diastole, when the arterial pressure is generally lower, will be a more specific indicator that a significant stenosis or narrowing is present.

Breath sounds may also provide considerable information about pulmonary pathology. In general, breath sounds caused by air rushing into and out of the lungs during respiration tend to be most coarse over the trachea and major bronchi and much finer and softer over the peripheral lung fields. Pathologic processes such as consolidation (as might occur with pneumonia) may increase the transmission of coarser upper airway sounds in the lung periphery, whereas other processes such as fluid gathering around the lung (pleural effusion) may decrease the sounds heard over an area. Increases in lung water, as might occur with heart failure as well as other pulmonary conditions, produces an abnormal crackling sound at end-inspiration called rales.

The relationship between abnormal heart sounds, peripheral vessel sounds, and breath sounds and underlying physical pathologies has long been appreciated by cardiologists.

However, clinical auscultation (examination by listening to body sounds) is an extremely difficult skill to master. The heart sounds are low pitched and close together, and it is difficult for humans to separate sounds out or remember sounds accurately. Even when auscultation is performed expertly, the data derived from the examination is expressed semi-quantitatively at best in the form of a note in the patient's file. No record of the actual data is available for further analysis or comparison with data from prior or subsequent examinations, or between observers.

A variety of inventions have been developed to assist physicians and other care givers with auscultation. None of these devices has been successful, due to several disadvantages discussed below. It is known in the art to provide a slowed down audio signal of a heart beat. See, for example U.S. Pat. No. 4,528,689 by Katz. It is also known to use an electronic stethoscope to display heart sounds visually. See U.S. Pat. Nos. 5,213,108, 5,218,969, and 5,010,889 by Bredesen et al., 5,025,809 by Johnson et al., 4,765,321 by Mohri, 4,254,302 by Walsh, 4,594,731 by Lewkowiez and 4,362,164 by Little. Some of these references discuss computer assisted diagnosis based on the heart sounds. It is also known to take frequency domain (e.g. fast Fourier transform) data of the heart sounds in order to aid in diagnosis. See, for example, U.S. Pat. Nos. 4,792,145 by Eisenberg et al., 5,301.679 by Taylor, 5,002,060 by Nedivi, and 4,720,866 by Elias et al.

None of these inventions are useful in normal diagnostic situations, because they do not provide any effective means of separating background noise, emanating from within the body or external to the body, from the body sounds to be analyzed. In addition, these inventions do not provide quantitative timing comparisons between body sounds, respiratory cycle, and electrical impulse.

SUMMARY OF THE INVENTION

An object of the present invention is to provide analysis of body sounds in normal diagnostic situations.

In order to accomplish this object, apparatus is provided for collection of body sounds such as heart sounds, peripheral vessel sounds or breath sounds. The body sound data is digitized, converted to frequency data, processed to remove small differences in timing, and signal averaged. This preserves frequency information while eliminating background noise.

The body sounds may be sorted according to respiratory phase and gated to the QRS complex of the ECG, or to other aspects of the ECG tracing such as the P and T waves. Generally, the signal averaged data is displayed visually to the operator for the purpose of allowing the operator to make a diagnosis. In addition, a computer algorithm may suggest diagnoses or further maneuvers for the operator to perform to further assist in differentiating the etiology of the sounds heard.

The data may be saved as a historical report or compared to previous patient data.

Those having normal skill in the art will recognize the foregoing and other objects, features, advantages, and applications of the present invention from the following, more detailed, description of the preferred embodiments as illustrated in the accompanying drawings.

BRIEF DESCRIPTION OF THE DRAWINGS

FIG. 9 is a chart showing an example of a diagnostic approach taken by the signal processor and analyzer of FIG. 3, when analyzing heart sounds.

FIG. 10 is a chart showing an example of a diagnostic approach taken by the signal processor and analyzer of FIG. 3, when analyzing breath sounds.

FIG. 11 is a chart showing an example of a diagnostic approach taken by the signal processor and analyzer of FIG. 3, when analyzing peripheral vessel sounds.

DETAILED DESCRIPTION OF THE PREFERRED EMBODIMENT

Figure 1:
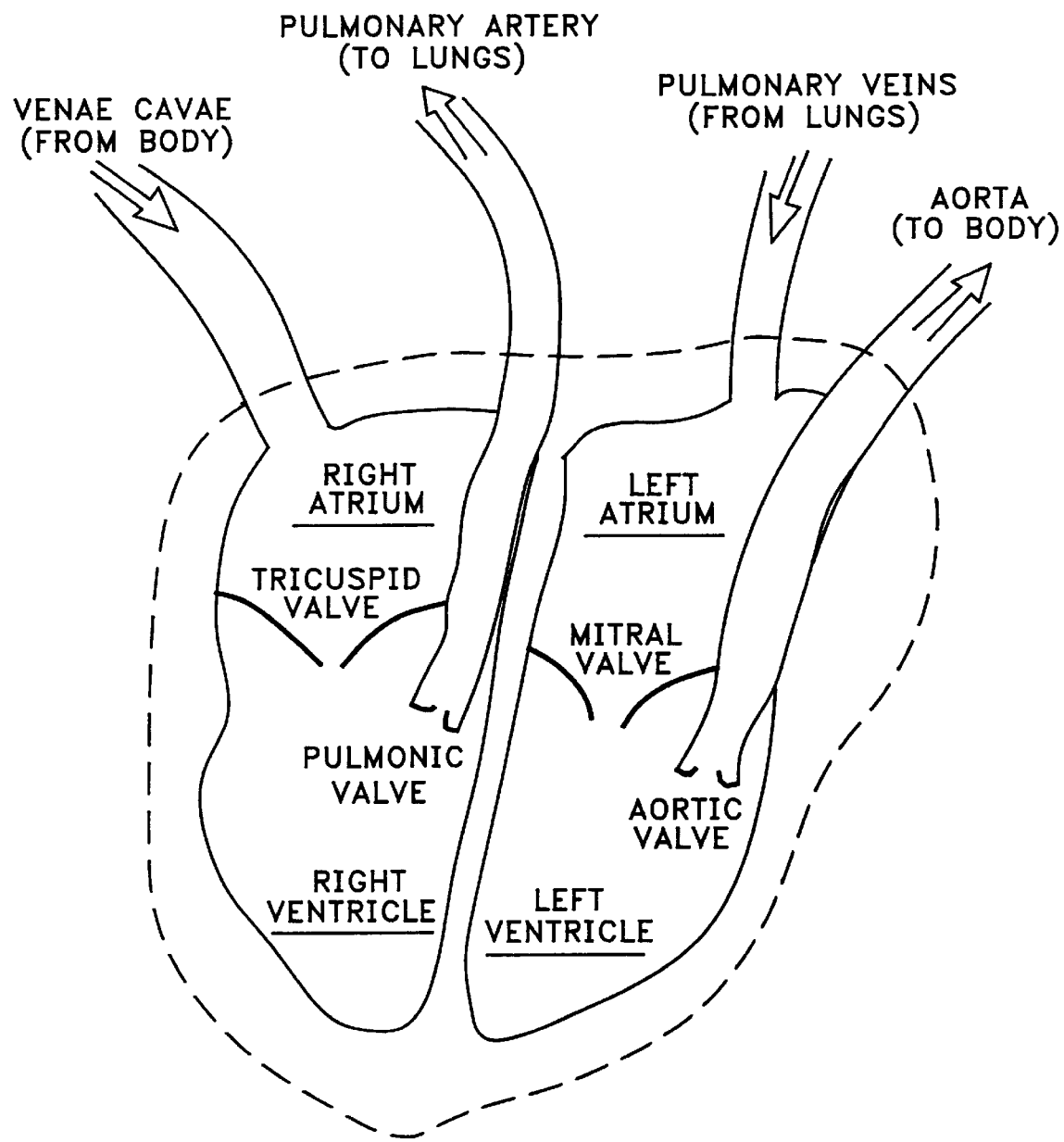
FIG. 1 is a schematic representation of a normal human heart.
Figure 2:
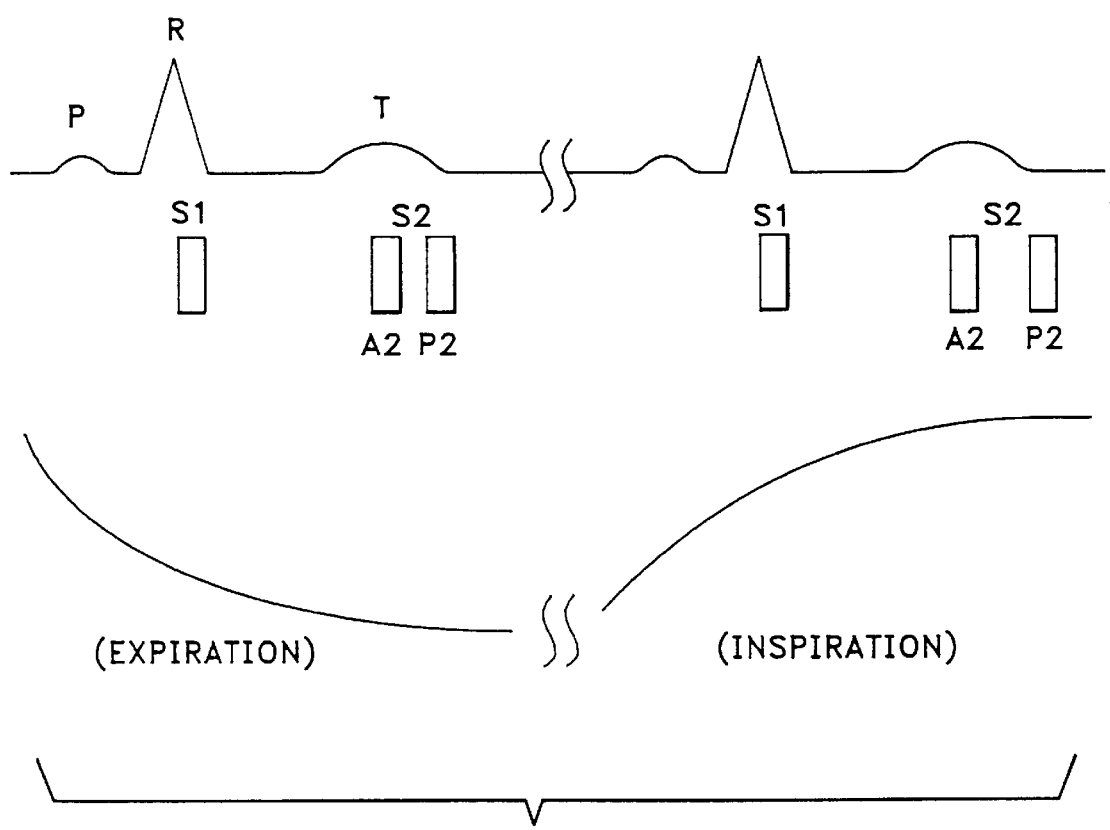
FIG. 2 shows the relationship between the electrical impulse controlling the heartbeat, the respiratory cycle, and normal heart sounds.
Figure 3:
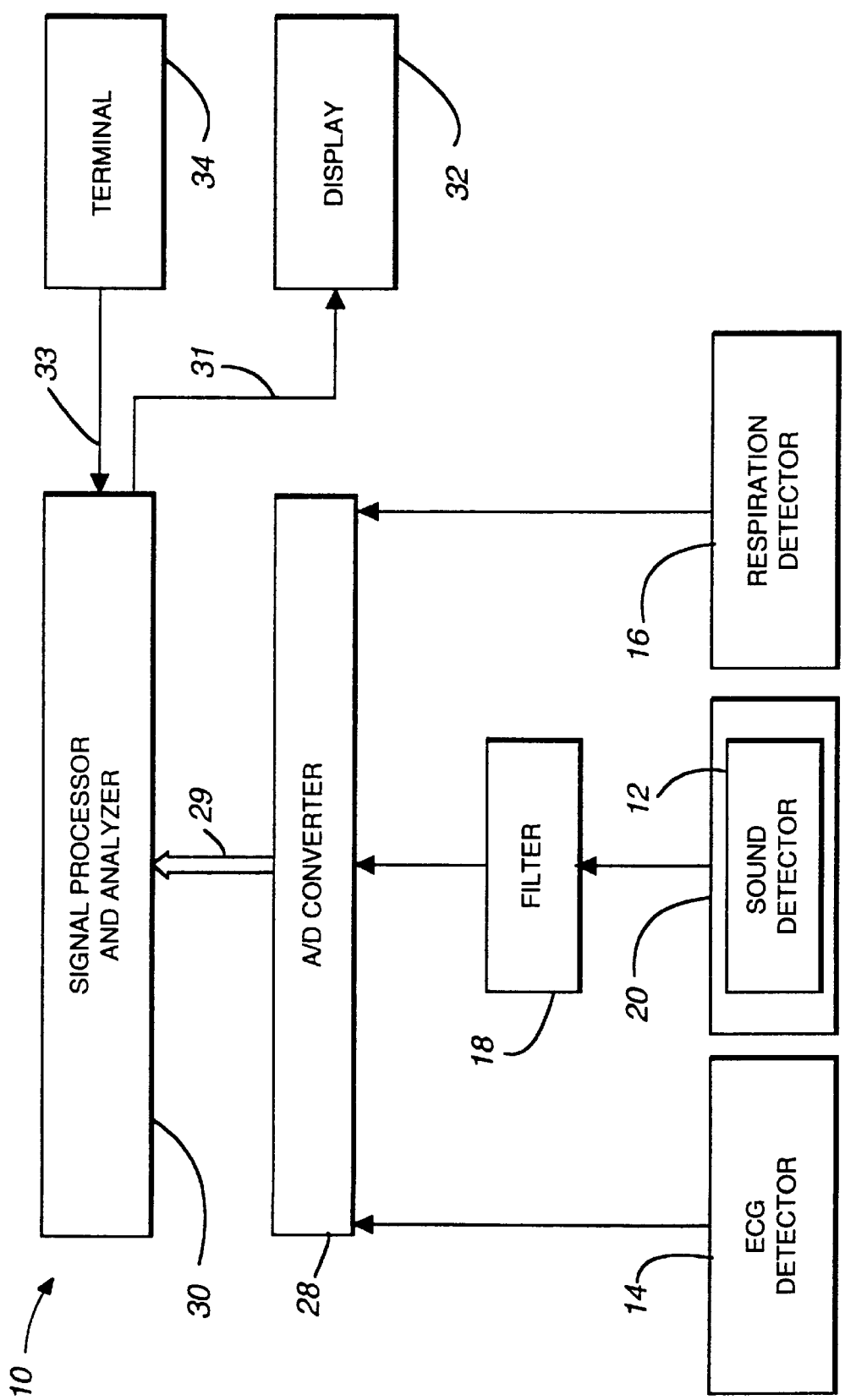
FIG. 3 is a functional block diagram showing the main components of a body sound analyzer in accordance with the present invention.

FIG. 3 is a functional block diagram showing the main components of a body sound analyzer 10 in accordance with the present invention. Body sounds which may be analyzed by the analyzer 10 include heart sounds, peripheral vessel sounds, and breath sounds. Depending upon which sounds are to be analyzed, some of the elements of analyzer 10 may be unnecessary. For example, when heart sounds or peripheral vessel sounds are being analyzed, the sounds, ECG, and respiration are detected simultaneously and analyzed as a group, because signal processor and analyzer 30 will sort the sounds according to respiratory phase and gate the sounds using the QRS complex (or some other aspect) of the ECG. When analyzing breath sounds, on the other hand, only the sound detector 12 and respiration detector 16 are used.

Generally, sound detector 12 is a conventional microphone assisted stethoscope having sound shielding 20. Conventional filtering may be accomplished by filter 18, and the output signal is provided to analog to digital converter (A/D converter) 28. ECG detector 14 is conventional. ECG detector 14 provides electrical heart signals to A/D converter 28. Respiration detector 16 is conventional and provides respiration data to A/D converter 28.

A/D converter 28 converts the analog body sounds, ECG and respiration signals into digital signals 29 for processing by signal processor and analyzer 30. Signal processor and analyzer 30 could be a computer or a microprocessor of various types. One convenient configuration is to have processor 30 be part of a laptop computer with display 32 being the monitor of the laptop and terminal 34 being the keyboard and monitor of the laptop as well. Another configuration which may be implemented is to use IR or RF transmission from the isolation amplifiers to a desk or laptop computer at some distance for processing and display. The functions performed by signal processor and analyzer 30 are shown in detail in FIGS. 4–7. Visual data and text provided by signal processor and analyzer 30 are displayed on display 32. Examples of the displays generated by processor 30 are shown in FIGS. 8A–8E. The physician or other care giver using body sound analyzer 10 controls the signal processor and analyzer 30 via terminal 34.

Figure 4:
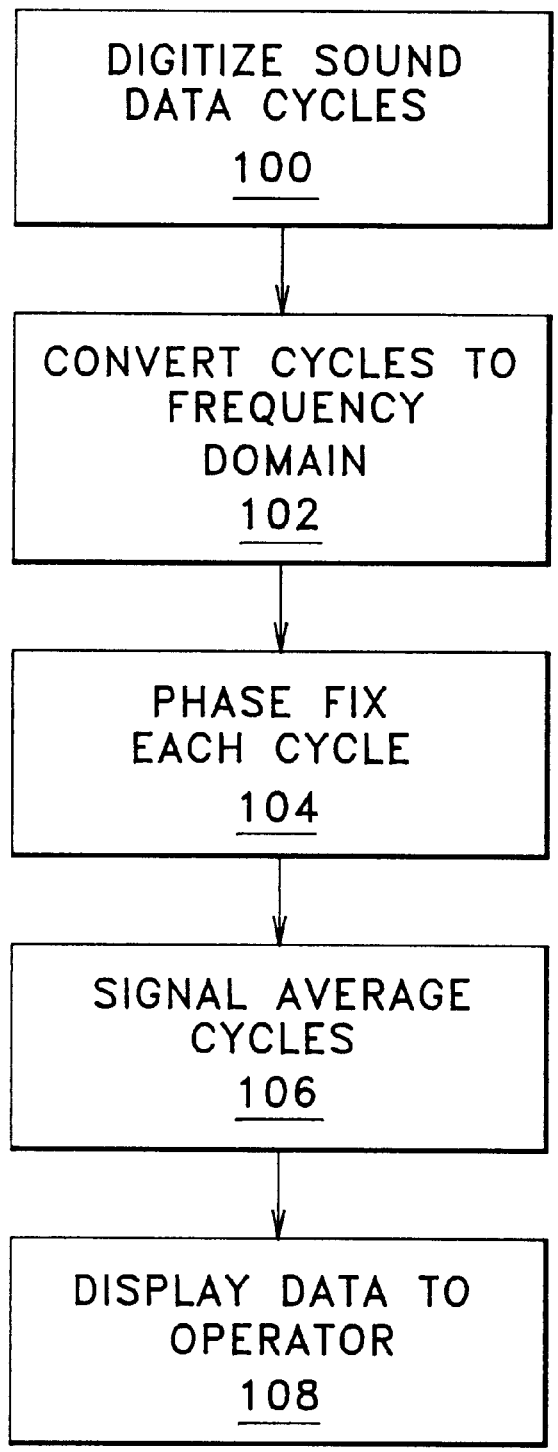
FIG. 4 is a high level flow diagram showing the process accomplished by the A/D converter and signal processor and analyzer of FIG. 3, applicable to a variety of cyclical body sounds.

FIG. 4 is a flow diagram showing the basic processes accomplished by A/D converter 28 and signal processor and analyzer 30 of FIG. 3. A/D converter 28 digitizes the body sound data, which consists of a predefined number of cycles, comprising heart beats, breaths, vessel sounds, or other cyclical body sounds in step 100. Processor and analyzer 30 converts each cycle to the frequency domain in step 102, for example by implementing a fast Fourier transform (FFT). Alternatively, a wavelet transform or any other time to frequency transformation might be employed. In step 104, a magnitude calculation or power calculation is performed on each frequency transformed cycle, to "phase fix" the cycles, or remove small differences in timing between the different cycles. The term "phase fix" is used herein to describe the process of adjusting for differences in the phase of frequency transformed sounds brought out by small timing differences, by using mathematical manipulations which make all signals positive within a given time window (e.g. magnitude or power calculation).

In step 106, processor and analyzer 30 signal averages the frequency transformed, phase fixed cycles. Finally, in step 108, the signal averaged data is displayed for an operator. Steps 102 through 106 would always be performed. Step 100 might be skipped if the operator were analyzing previously stored digital data. Step 108 might be skipped if the operator were storing the signal averaged data for future analysis.

Figure 5:
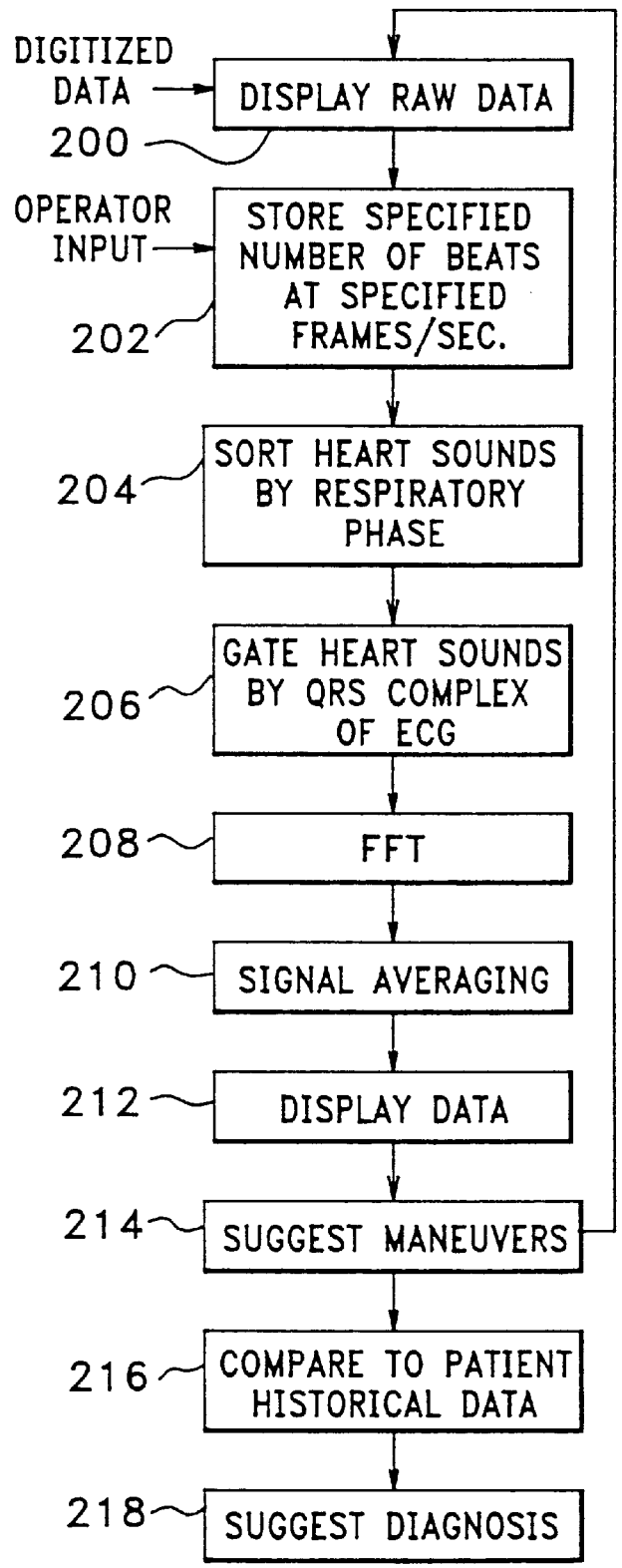
FIG. 5 is a flow diagram showing the process accomplished by the signal processor and analyzer of FIG. 3, when analyzing heart sounds.
Figure 6:
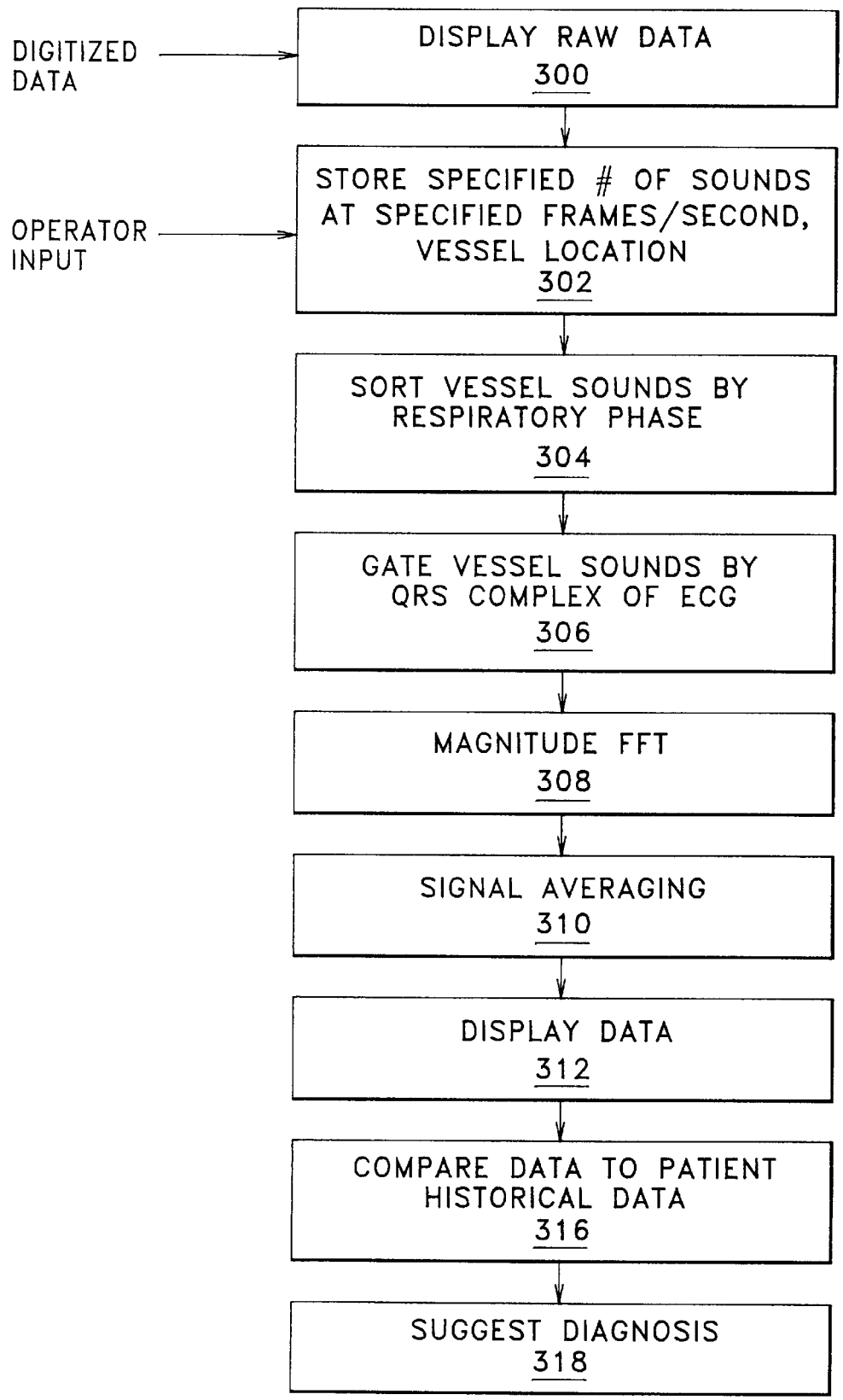
FIG. 6 is a flow diagram showing the process accomplished by the signal processor and analyzer of FIG. 3, when analyzing peripheral vessel sounds.
Figure 7:
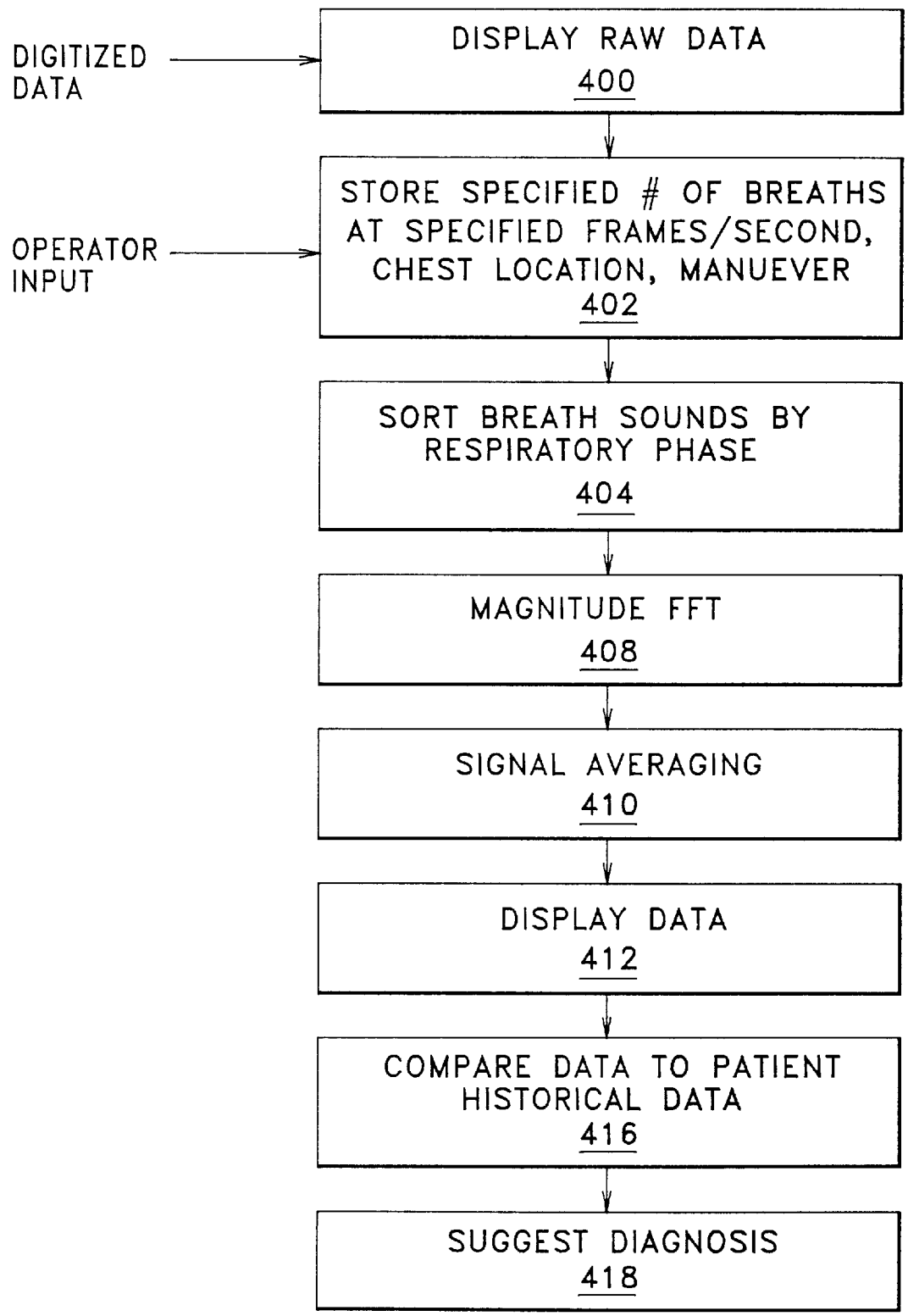
FIG. 7 is a flow diagram showing the process accomplished by the signal processor and analyzer of FIG. 3, when analyzing breath sounds.

FIG. 4 is a very general, high level flow diagram describing the operation of body sound analyzer 10 for analyzing a variety of body sounds. FIGS. 5–7 are more detailed flow diagrams showing preferred operation of the signal processor and analyzer for specific body sounds.

FIG. 5 is a flow diagram showing the preferred process accomplished by signal processor and analyzer 30 of FIG. 3, when analyzing heart beat sounds. Processor and analyzer 30 begins in step 200 by displaying the raw heart sounds data received from A/D converter 28 in amplitude versus time format on display 32 via signal 31. When the operator is content with the displayed signal, the operator signals processor 30 via signal 33 from terminal 34 to begin storing data 29. The operator may specify the number of beats to be stored, the number of frames per second to store and the place of detection and maneuver, or these may be predetermined parameters stored within processor 30. Processor 30 stores the next specified number of beats by counting the QRS complex signals on the ECG signal in step 202.

Processor 30 sorts the heart beat sounds into two sets, according to respiratory phase, in step 204. Next, in step 206, processor 30 gates the stored heart sounds using the QRS component, so all of the heart sounds are roughly synchronized. In step 208, the heart beat sounds are individually frequency transformed and phase fixed, for example by performing a magnitude FFT calculation. Taking the magnitude FFT of each heart sound prevents differences in timing between successive heart sounds from causing data loss in the signal averaging step. Step 210 accomplishes the signal averaging of the FFT signals. All of the inspiration beats are averaged separately from all of the expiration beats. Signal averaging generally improves signal to noise ratio as square root of n, where n is the number of acquisitions (heart beat sounds stored). The improvement in signal to noise ratio in the present invention will approach this level, but will not quite reach it because part of the improvement in the conventional scheme is due to cancellation of positive and negative noise. The improvement is sufficient so that the acquisition does not need to occur in ideal conditions in a sound proofed room, but can be accomplished in normal doctor's office or hospital settings having a significant amount of background noise. The two averaged sets are displayed in step 212.

Signal processor and analyzer 30 may suggest that the operator perform other maneuvers to collect more data in step 214. If this occurs, process returns to step 200 to collect and process a second set of heart sound data. In any case, once all of the data is collected, it is compared to historical patient data in step 216. In step 218, processor 30 suggests a diagnosis. FIG. 9 shows examples of how processor 30 can accomplish the steps of suggesting maneuvers and diagnosis.

FIG. 6 is a flow diagram showing the process accomplished by signal processor and analyzer 30, when analyzing peripheral vessel sounds. Processor and analyzer 30 begins in step 300 by displaying the raw peripheral vessel sounds data received from A/D converter 28 in amplitude versus time format on display 32 via signal 31. When the operator is content with the displayed signal, the operator signals processor 30 via signal 33 from terminal 34 to begin storing data 29. The operator may specify the number of beats to be stored, the number of frames per second to be stored and the vessel location, or these may be predetermined parameters stored within processor 30. Processor 30 stores the next specified number of sounds by counting the QRS complex signals on the ECG signal in step 302.

Processor 30 sorts the vessel sounds into two sets, according to respiratory phase, in step 304. Next, in step 306, processor 30 gates the stored heart sounds using the QRS component. In step 308, the heart beat sounds are individually frequency transformed and phase fixed, for example by performing a magnitude FFT calculation. Step 310 accomplishes the signal averaging of the magnitude FFT signals. The inspiration sounds are averaged separately from the expiration sounds. The two averaged sets are displayed in step 312. The data is compared to historical patient data in step 316. In step 318, processor 30 suggests a diagnosis.

FIG. 7 is a flow diagram showing the process accomplished by signal processor and analyzer 30, when analyzing breath sounds. Processor and analyzer 30 begins in step 400 by displaying the raw breath sounds data received from A/D converter 28 in amplitude versus time format on display 32 via signal 31. When the operator is content with the displayed signal, the operator signals processor 30 via signal 33 from terminal 34 to begin storing data 29. The operator may specify the number of breaths to be stored, the number of frames per second to store and the chest location, or these may be predetermined parameters stored within processor 30. Processor 30 stores the next specified number of sounds by counting the respiration detector signals in step 402.

Processor 30 sorts the breath sounds into two sets, according to respiratory phase, in step 404. In step 408, the breath sounds are individually frequency transformed and phase fixed, for example by performing a magnitude FFT calculation. Step 410 accomplishes the signal averaging of the magnitude FFT signals. The inspiration sounds are averaged separately from the expiration sounds. The two averaged sets are displayed in step 412. The data is compared to historical patient data in step 416. In step 418, processor 30 suggests a diagnosis.

Figure 8A:
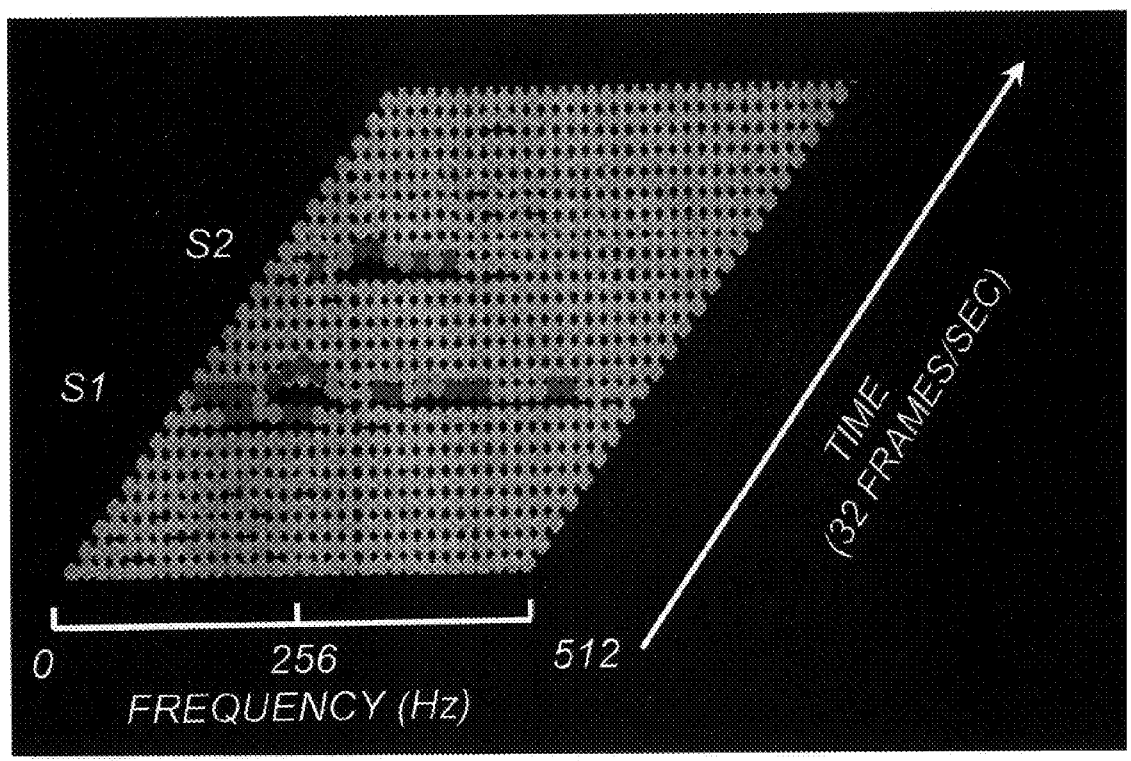
FIGS. 8A, 8B, 8C, 8D and 8E show displays produced by the signal processor and analyzer of FIG. 3, when analyzing heart sounds.

FIGS. 8A, 8B, 8C, 8D and 8E show displays produced by the signal processor and analyzer of FIG. 3, when analyzing heart sounds. FIG. 8A shows how the display of the heart sounds of a patient with a normal heart might look. S1 and S2 are nicely separated, with no extra sounds or murmurs appearing. The x-axis shows the frequency of the sounds, and the y-axis, along with the color of the dots, indicates the intensity of the sound. Red dots indicate the highest intensity, followed by green dots, then blue, then white. Intensity is also indicated by the height of the dots. Time is displayed along the diagonal.

Figure 8B:
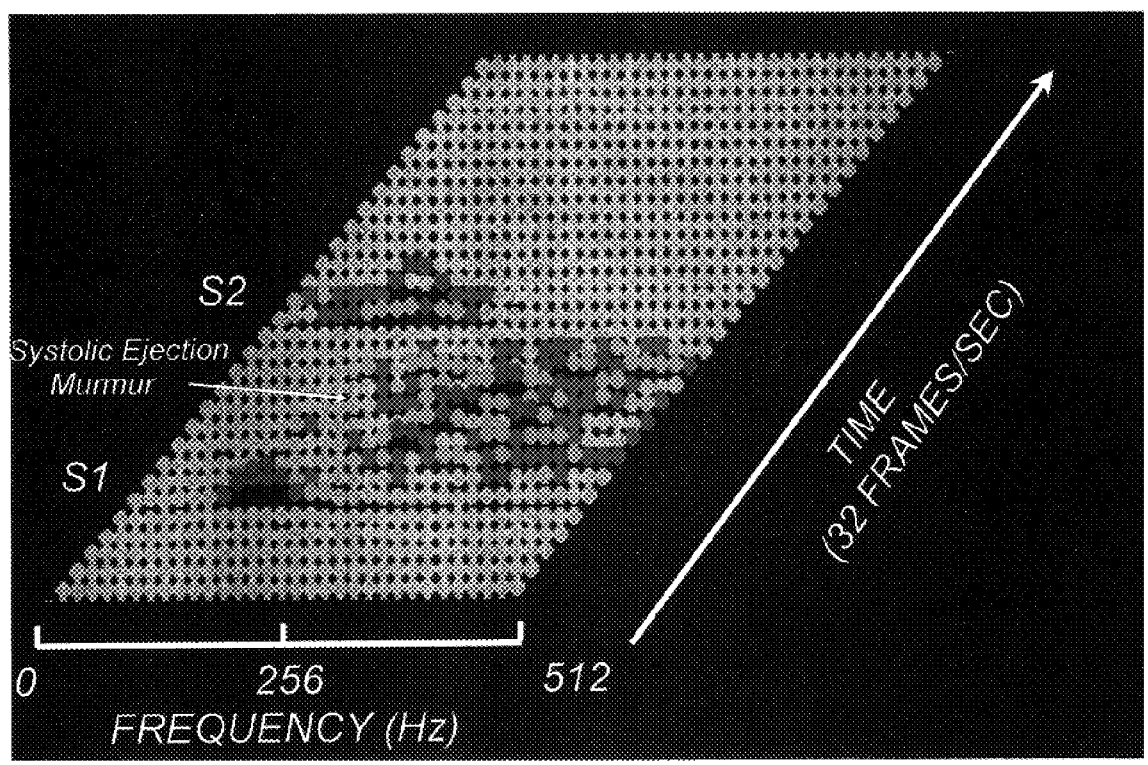

FIG. 8B shows a representative tracing of the heart sounds of a patient with aortic stenosis. Aortic stenosis is generally associated with a soft A2 sound, with a high-pitched extra sound (systolic ejection click) in early systole and an associated crescendo-decrescendo systolic murmur between S1 and S2. See FIG. 9. FIG. 8B demonstrates how the murmur begins after S1 and ends before S2. Moreover, it is clear that the intensity and the frequency of the murmur are not constant.

Figure 8C:
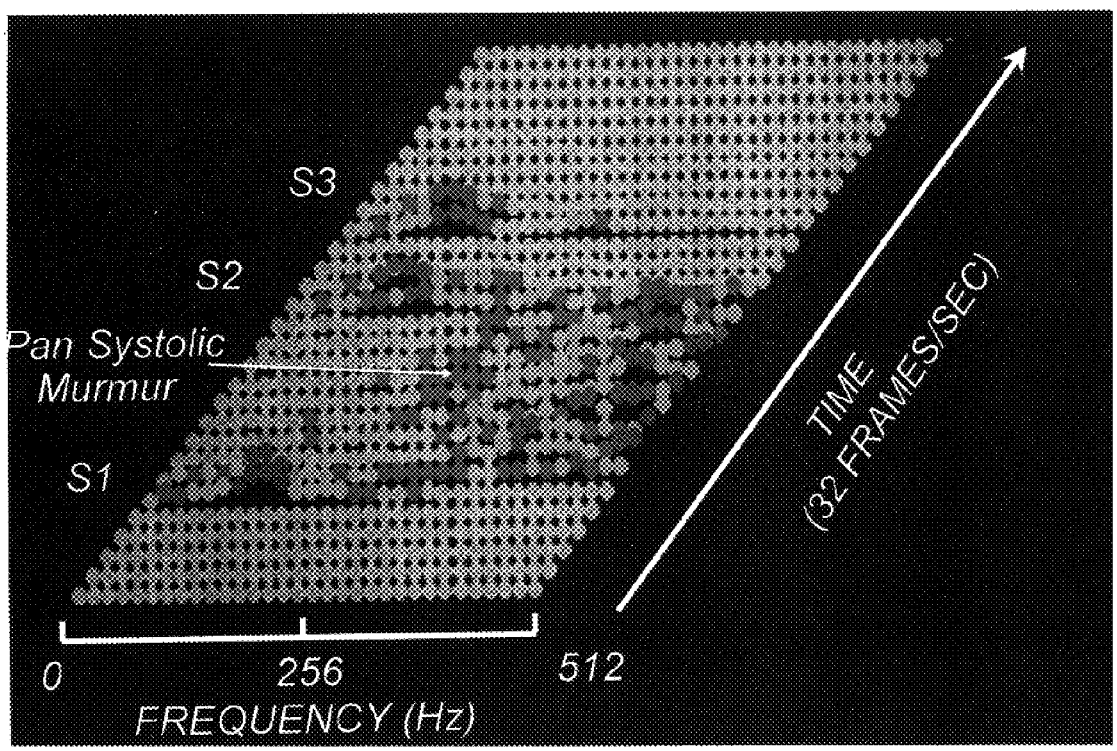

FIG. 8C shows a representative tracing of the heart sounds of a patient with mitral regurgitation. Mitral regurgitation is generally associated with a soft S1 sound and an associated holo-systolic murmur from S1 to S2, and is confirmed by hand grip making the murmur louder. FIG. 8C illustrates the presence of the murmur throughout systole (i.e. from S1 to S2).

Figure 8D:
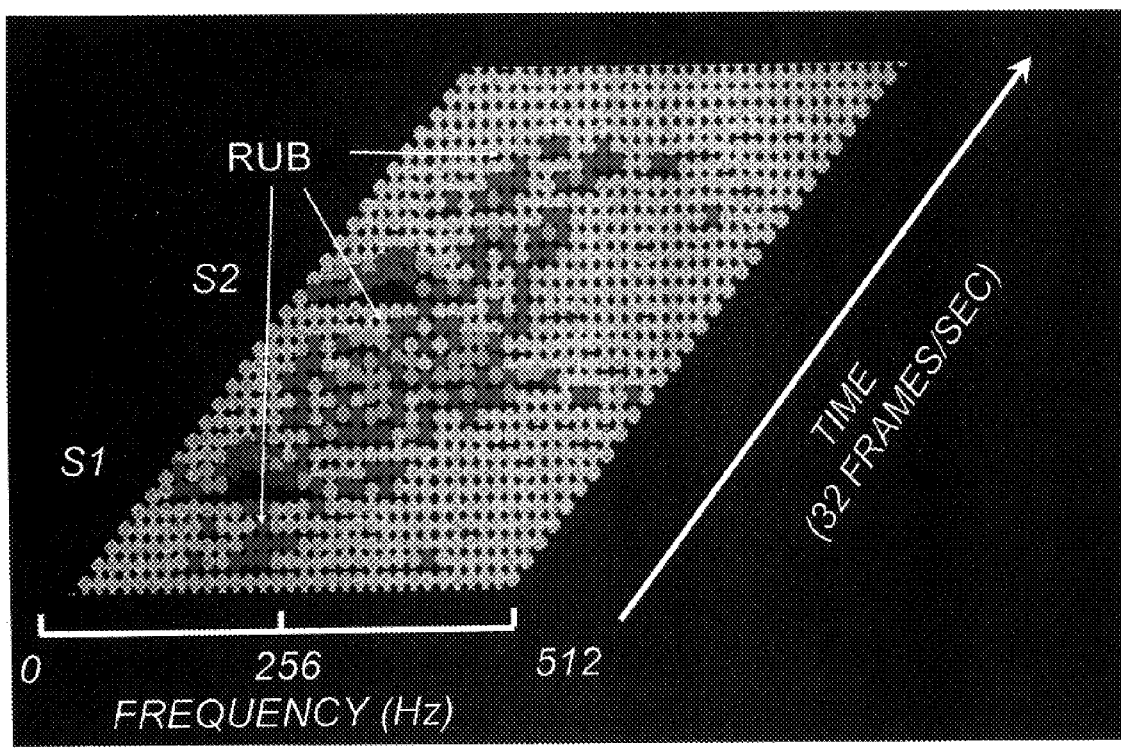

FIG. 8D shows a representative tracing of the heart sounds of a patient having a pericardial friction rub. This sound results from rubbing of an inflamed pericardium during the cardiac cycle. Although this may sound like systolic and diastolic murmurs, FIG. 8D confirms a unique frequency signature to this sound.

Figure 8E:
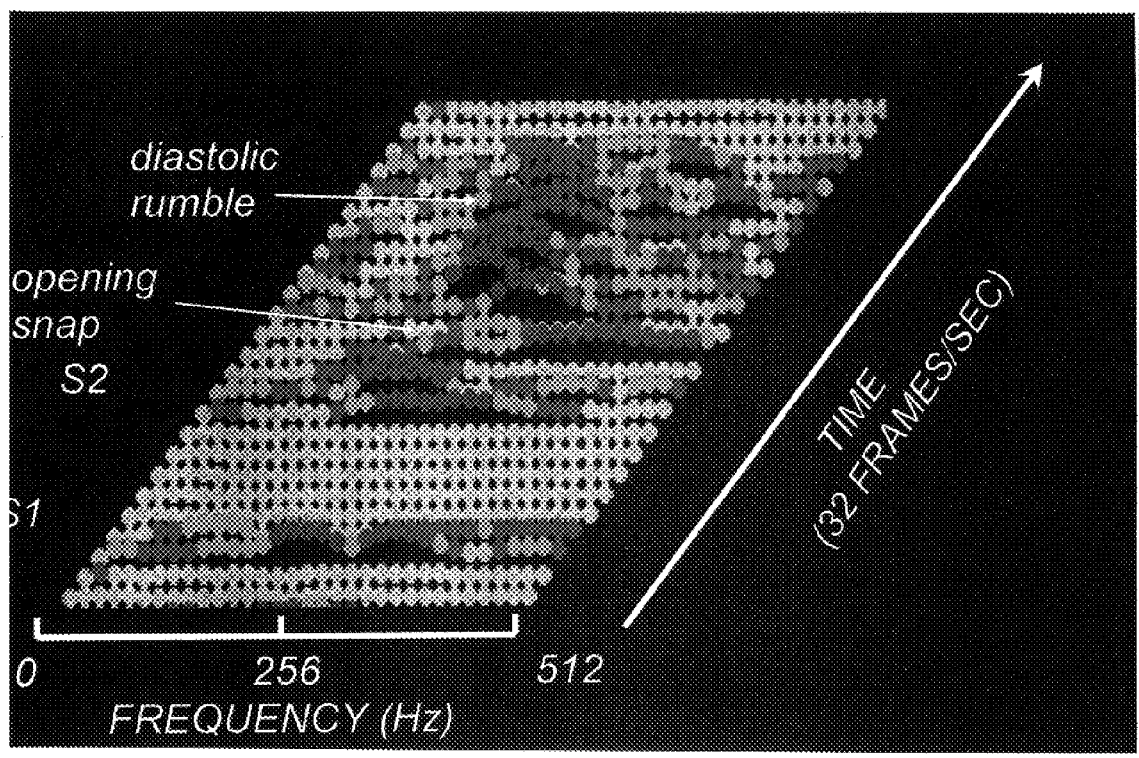

FIG. 8E shows a representative display of the heart sounds of a patient with mitral stenosis. Mitral stenosis is generally associated with a loud M1 sound, a low pitched decrescendo associated murmur in early diastole and opening snap in early diastole (see FIG. 9). FIG. 8E shows all of these features.

FIG. 9 is a chart showing an example of a diagnostic approach which could be taken by the signal processor and analyzer 30 in suggesting maneuvers and diagnoses to the operator, when analyzing heart sounds. First, abnormal sounds are divided into abnormal sounds, murmurs, and other extra heart sounds. Next, sounds are classified according to their timing in the heart sound cycle, and whether the timing is consistent or not. Then the frequency or pitch of the sound is added as a factor. Respiratory phase is examined as a factor. Signal processor and analyzer 30 then suggests a lesion based upon these factors. If a different maneuver will help confirm the diagnosis, signal processor and analyzer 30 displays a request for the user to perform this maneuver. Those skilled in the art will appreciate that computer assisted diagnosis could be based upon these characteristics.

FIG. 10 is a chart showing an example of a diagnostic approach which could be taken by the signal processor and analyzer 30 in suggesting diagnoses to the operator, when analyzing breath sounds. Sounds are classified according to their timing in the breathing cycle. Then the frequency or pitch of the sound is added as a factor. Location of sound detection is examined as a factor. Signal processor and analyzer 30 then suggests a diagnosis based upon these factors. Methods of confirming the diagnosis may also be suggested. Those skilled in the art will appreciate that computer assisted diagnosis could be based upon these characteristics.

FIG. 11 is a chart showing an example of a diagnostic approach which could be taken by the signal processor and analyzer 30 in suggesting diagnoses to the operator, when analyzing peripheral vessel sounds. Sounds are classified according to their timing in the heart beat cycle. Then the frequency or pitch of the sound is added as a factor. Location of sound detection is examined as a factor. Signal processor and analyzer 30 then suggests a diagnosis based upon these factors. Methods of confirming the diagnosis may also be suggested. Those skilled in the art will appreciate that computer assisted diagnosis could be based upon these characteristics.

Figure 12:
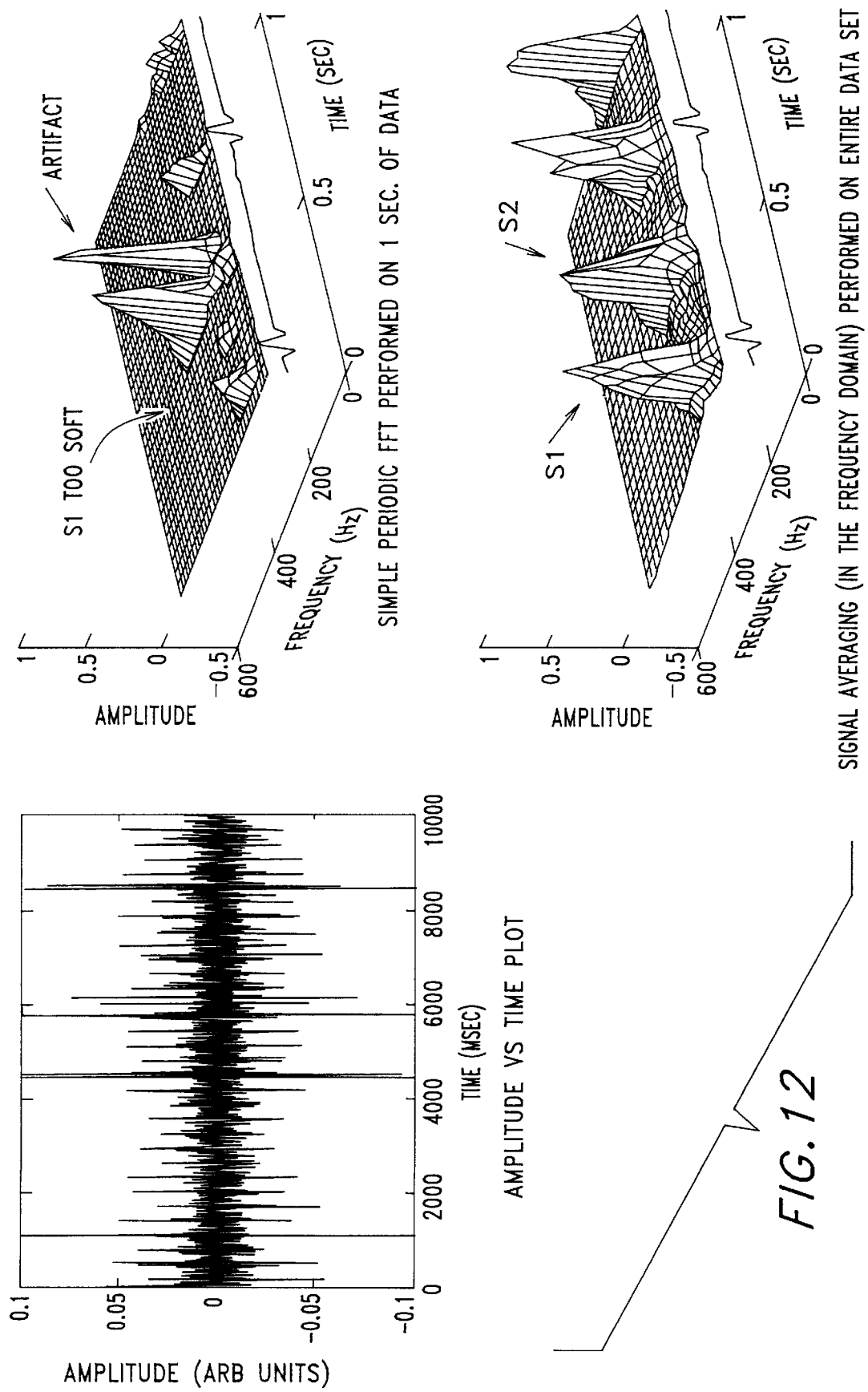
FIG. 12 shows the effect on heart beat sounds of signal averaging in the frequency domain according to the present invention.

FIG. 12 shows the effect on heart beat sounds of signal averaging in the frequency domain. The plot in the upper left hand corner shows amplitude of sound versus time for one second of data (no averaging). The plot in the upper right hand corner shows a three dimensional plot indicating amplitude versus time and frequency of the one second sample. A large artifact is evident. The plot on the bottom shows one second of data obtained by signal averaging an entire data set in the frequency domain, after phase fixing. The artifact has disappeared, and a very clean signal is obtained.

In addition to the obvious application for screening and diagnosis of anatomic and functional heart disease, another extremely useful capability of the present invention is following the natural history as well as treatment response once cardiac abnormalities have been documented and characterized. For example, suppose a patient's mitral stenosis was detected by the present invention and the mitral valve area was quantified with an additional anatomic test (e.g. echocardiography, costing around $1000 per study). The progression of the stenosis could be followed by the present invention using the timing between the opening snap (OS) and aortic closure (A2) as well as the pitch and intensity of the diastolic murmur. Once the present invention determined that the severity of the lesion had increased to the point which warranted surgical intervention, a follow-up echocardiogram could be performed to confirm this conclusion. The documentation and direct quantification of measurements made with the present invention obviates the need for frequently repeated anatomic studies, saving the patient time and money.

While the exemplary preferred embodiments of the present invention are described herein with particularity, those skilled in the art will appreciate various changes, additions, and applications other than those specifically mentioned, which are within the spirit of this invention. For example, some physicians may possess greater skill at interpreting the graphical displays generated by the present invention. Given the digital nature of the invention, it would be possible to transfer the data over telephone lines to obtain consultation with expert interpreters as well to allow for the user to perform comparison of studies which were acquired at different times and/or different places and stored at a remote site.

What is claimed is:

1. Apparatus for analyzing body sounds utilizing body sound data collected from a patient, said apparatus comprising:

means for storing a plurality of cycles of data representing a body sound;

means for converting each cycle to the frequency domain;

means for phase fixing each frequency converted cycle;

means for signal averaging the phase fixed cycles; and means for providing the averaged signals to a user.

2. The apparatus of claim 1, further including means for visually displaying the averaged signals.

3. The apparatus of claim 1 wherein the cycles of data represent heart beat sounds, said apparatus further including:
   means for gating the cycles according to ECG data collected from the patient.

4. The apparatus of claim 3, further including:
   means for sorting said cycles according to respiratory phase;
   wherein said means for signal averaging the phase fixed cycles signal includes averaging the phase fixed cycles separately according to respiratory phase.

5. The apparatus of claim 3, further including:
   means for providing a signal to the user indicating suggested maneuvers to be performed on said patient.

6. The apparatus of claim 3, further including:
   means for comparing the averaged signals to a historical database for said patient.

7. The apparatus of claim 3, further including:
   means for selecting a suggested patient diagnosis based upon the averaged signals; and
   means for providing a signal to the user indicating the selected patient diagnosis.

8. The apparatus of claim 1 wherein the cycles of data represent peripheral vessel sounds and which also uses ECG data collected from the patient, said apparatus further including:
   means for gating the cycles according to the ECG data.

9. The apparatus of claim 8 which also utilizes respiratory phase data collected from the patient, and further including:
   means for sorting said cycles according to respiratory phase;
   wherein said means for signal averaging signal averages the frequency converted, phase fixed cycles separately according to respiratory phase.

10. The apparatus of claim 8, further including:
    means for comparing the averaged signals to a historical database for said patient.

11. The apparatus of claim 8, further including:
    means for selecting a suggested patient diagnosis based upon the averaged signals; and
    means for providing a signal to the user of said apparatus, said signal for indicating the selected patient diagnosis.

12. The apparatus of claim 1 wherein the cycles of data represent breath sounds and which also utilizes respiration phase data collected from the patient, and further including:
    means for gating said breath sounds according to respiratory phase.

13. The apparatus of claim 12, further including:
    means for comparing the averaged signals to a historical database for said patient.

14. The apparatus of claim 12, further including:
    means for selecting a suggested patient diagnosis based upon the averaged signals; and
    means for providing a signal to the user of said apparatus, said signal for indicating the selected patient diagnosis.

15. A method of analyzing body sounds utilizing body sound data collected from a patient, said method comprising:
    storing a plurality of cycles of data representing a body sound;
    converting each cycle to the frequency domain;
    phase fixing each frequency converted cycle;
    signal averaging the phase fixed cycles; and
    providing the averaged signals to a user.

16. The method of claim 15, further including
    sorting said cycles according to respiratory phase.

17. The method of claim 15, further including
    selecting a suggested patient diagnosis based upon the averaged signals; and
    providing a signal to the user indicating the selected patient diagnosis.

18. The method of claim 15, said method further including
    gating the cycles according to ECG data.

19. The method of claim 18 further including
    providing a signal to the user indicating suggested maneuvers to be performed on said patient.

20. Method of claim 15, wherein the cycles represent peripheral vessel sounds and which also utilizes the ECG data from the patient, said method further including the step of:
    gating the cycles according to the ECG data.

21. The method of claim 15, wherein the cycles represent breath sounds.

22. Apparatus for analyzing body sounds utilizing body sound data and respiratory phase data collected from a patient, said apparatus comprising:
    means for storing a plurality of cycles of data representing a body sound;
    means for sorting said cycles according to respiratory phase;
    means for converting each cycle to the frequency domain;
    means for phase fixing each frequency converted cycle;
    means for signal averaging the phase fixed cycles; and
    means for providing the averaged signals to a user.

23. The apparatus of claim 22, further including means for visually displaying the averaged signals.

24. The apparatus of claim 22, further including means for providing a signal to the user for indicating suggested maneuvers to be performed on said patient.

25. The apparatus of claim 22, further including means for comparing the averaged signals to a historical database for said patient.

26. The apparatus of claim 22, further including means for selecting a suggested patient diagnosis based upon the averaged signals and means for providing a signal to the user of said apparatus indicating the selected patient diagnosis.

27. The apparatus of claim 22, further including means for gating the cycles according to ECG data.

28. A method of analyzing body sounds utilizing body sound and respiratory phase data collected from a patient, said method comprising:
    storing a plurality of cycles of data representing a body sound;
    converting each cycle to the frequency domain;
    sorting said cycles according to respiratory phase;
    phase fixing each frequency converted cycle;
    signal averaging the phase fixed cycles; and
    providing the averaged signals to a user.

29. The method of claim 28, further including selecting a suggested patient diagnosis based upon the averaged signals and providing a signal to the user that indicates the selected patient diagnosis.

30. The method of claim 28, wherein the cycles represent heart beat and said method further including gating the cycles according to ECG data collected from the patient.

31. The method of claim 30 further including providing a signal to the user indicating suggested maneuvers to be performed on the patient.

* * * * *